US007718395B2

(12) United States Patent
Carling

(10) Patent No.: US 7,718,395 B2
(45) Date of Patent: May 18, 2010

(54) MONITORING CLEANING OF SURFACES

(75) Inventor: Philip C. Carling, Hingham, MA (US)

(73) Assignee: Kleancheck Systems, LLC, Hingham, MA (US)

( * ) Notice: Subject to any disclaimer, the term of this patent is extended or adjusted under 35 U.S.C. 154(b) by 439 days.

(21) Appl. No.: 11/335,905

(22) Filed: Jan. 19, 2006

(65) Prior Publication Data

US 2006/0223731 A1 Oct. 5, 2006

Related U.S. Application Data

(60) Provisional application No. 60/666,391, filed on Mar. 30, 2005.

(51) Int. Cl.
*G01N 1/00* (2006.01)
*G01N 1/34* (2006.01)
*C11D 17/00* (2006.01)
*C12Q 1/14* (2006.01)
*C12Q 1/22* (2006.01)

(52) U.S. Cl. .......................... 435/36; 435/31; 435/40.5; 435/252.4; 435/882; 435/883; 134/42; 510/56

(58) Field of Classification Search ................ 435/8, 435/31, 36, 40.5, 252.4, 882, 883, 885; 134/42; 510/56

See application file for complete search history.

(56) References Cited

U.S. PATENT DOCUMENTS

| | | | | |
|---|---|---|---|---|
| 2,600,221 | A | * | 6/1952 | Domingo .................... 134/18 |
| 3,309,274 | A | * | 3/1967 | Brilliant .................... 424/9.6 |
| 3,640,889 | A | | 2/1972 | Stewart |
| 3,716,488 | A | * | 2/1973 | Kolsky et al. ................. 442/93 |
| 5,084,327 | A | | 1/1992 | Stengel ....................... 428/206 |
| 5,116,533 | A | | 5/1992 | Grandmont et al. .... 252/301.36 |
| 5,203,638 | A | | 4/1993 | Redmond, Jr. ................. 401/17 |
| 5,453,120 | A | | 9/1995 | Rendino et al. .......... 160/19 B |
| 5,498,280 | A | | 3/1996 | Fistner et al. ............. 106/19 B |
| 5,900,067 | A | | 5/1999 | Jones ............................. 134/1 |
| 6,476,385 | B1 | | 11/2002 | Albert ......................... 250/302 |
| 6,524,390 | B1 | | 2/2003 | Jones ............................ 134/1 |
| 6,943,348 | B1 | | 9/2005 | Coffin, IV ................... 250/302 |
| 6,949,205 | B2 | | 9/2005 | Pendergrass ........... 252/301.36 |
| 2002/0192755 | A1 | * | 12/2002 | Francis et al. .............. 435/69.1 |
| 2003/0197122 | A1 | | 10/2003 | Faiola et al. ................ 250/302 |

OTHER PUBLICATIONS

Infectious Diseases Society of America, Bad bugs, no drugs. Available at: http://www.idsociety.org, pp. 1-35, Jul. 2004.

Byers K, et al., Disinfection of hospital rooms contaminated with Vancomycin-resistant *Enterococcus faecium*. Infect Control Hosp Epidemiol 1998;19:261-264.

Rutala, W. et al., Infection Control: the role of disinfection and sterilization. J Hosp Inf 1999;43(Suppl):43-55.

Fekety, R. et al., Epidemiology of antibiotic-associated colitis. Isolation of *Clostridium difficile* from the hospital environment. Am J Med.1981;70:906-908.

Rutala, W. et al., Environmental study of a methicillin-resistant *Staphylococcus aureus* epidemic in a burn unit. J Clin Micro. 1983; 18:(3);683-688.

Ansari, S. et al., Rotavirus survival on hands and transfer of infectious virus to animate and nonporous inanimate surfaces. J Clin Micro. 1988;26: 1513-1518.

Kaatz, G. et al., Acquisition of *Clostridium difficile* from the hospital environment. A J Epid. 1988;127:1289-1293.

McFarland, L. et al., Nosocomial acquisition of *Clostridium difficile* infection. N Eng J Med.1989;320:204-210.

Boyce, J. et al., Outbreak of multidrug-resistant *Enterococcus faecium* with transferable vanB Class Vancomycin resistance. J Clin Micro.1994:32:1148-1153.

Shay, D. et al., Epidemiology and mortality risk of Vancomycin-resistant enterococcal bloodstream infections. J Infect Dis 1995;172:993-1000.

Bonten, M. et al., Epidemiology of colonization of patients and environment with Vancomycin-resistant *Enterococci*. Lancet. 1996;348:1615-1619.

Samore, M. et al., Clinical and molecular epidemiology of sporadic and clustered cases of nosocomial *Clostridium difficile* Diarrhea. Am J Med.1996;100:32-40.

Lai, K. et al., Failure to eradicate vancomycin-resistant *Enterococci* in a university hospital and the cost of barrier precautions. Infect Control Hosp Epidemiol. 1998;19:647-52.

Donskey, C. et al., Effect of antibiotic therapy on the density of Vancomycin-resistant enterococci in the stool of colonized patients. N. Eng J Med. 2000;343:1925-1932.

Bures, S. et al., Computer keyboards, boards and faucet handles as reservoirs of nosocomial pathogens in the intensive care unit. AM J Infect Control. 2000; 28 465-71.

(Continued)

*Primary Examiner*—Jon P Weber
*Assistant Examiner*—Kailash C Srivastava
(74) *Attorney, Agent, or Firm*—Sunstein Kann Murphy & Timbers LLP

(57) ABSTRACT

A method for monitoring cleaning of a surface includes applying an amount of transparent indicator material to an area of a surface and measuring the amount of transparent indicator material remaining on the surface. The transparent indicator material may be fixed on the surface by drying and, when a fluorescent material, may be measured through exposure to ultraviolet radiation.

36 Claims, 14 Drawing Sheets

OTHER PUBLICATIONS

Ray, A. et al., Nosocomial transmission of Vancomycin-resistant *Enterococci* from surfaces. JAMA. 20, 2002; 287:1400-1401.

Oie, S. et al., Contamination of room door handles by methicillin-sensitive/methicillin-resistant *Staphylococcus aureus*. J Hosp Inf 2002;51:140-143.

Mayer, R. et al., Role of fecal incontinence in contamination of the environment with Vancomycin-resistant *Enterococci*. Am J Infect Control. 2003;31:(4);221-225 (Abstract Only).

Bhalla, A. et al., Acquisition of nosocomial pathogens on hands after contact with environmental surfaces near hospitalized patients. Infect Control Hosp Epidemiol. 2004;25:164-167.

Lemmen, S. et al., Distribution of multi-resistant gram-negative versus gram-positive bacteria in the hospital inanimate environment. J Hosp Infect.2004;56:191-197.

Christiansen, K. et al., Eradication of a large outbreak of a single strain of van B vancomycin-resistant *Enterococcus faecium* at a major Australian teaching hospital. Infect Control Hosp Epidemiol. 2004; 25: 384-390.

French, G. et al., Survival of nosocomial bacteria dried in air and killing by hydrogen peroxide vapour. Abstracts of the 44th Interscience Conference on Antimicrobial Agents and Chemotherapy; 2004:Washington, D.C.; p. 376 (abstr K-1602).

Boyce, J. et al., Environmental contamination due to methicillin-resistant *Staphylococcus aureus*: possible infection control implications. Infect Control Hosp Epidemiol.1997;18:622-627.

Davidson, C. et al., Evaluation of two methods for monitoring surface cleanliness—ATP bioluminescence and traditional hygiene swabbing. Luminescence 1999;14:33-38.

Griffith, C. et al., An evaluation of hospital cleaning regimes and standards. J Hosp Inf. 2000;45:19-28.

Stiefel, U. et al., Increased susceptibility to Vancomycin-resistant *Enterococcus* intestinal colonization persists after completion of anti-anaerobic antibiotic treatment in mice. Infect Control Hosp Epidemio 20041; 25:373-379.

Clarke, P. et al., Persistence of Vancomycin-resistant *Enterococci* (VRE) and other bacteria in the environment. Ir Med J Oct. 2001;94:(9).

French, G. et al., Tackling contamination of the hospital environment by methicillin resistant *Staphylococcus aureus* (MRSA): a comparison between conventional terminal cleaning and hydrogen peroxide vapour decontamination. J Hosp Infect. 2004; 57:31-37.

Edmond, M. et al., Vancomycin-resistant *Enterococcus faeciurn* bacteremia: Risk factors for infection. Clin Infect Dis.1995;20:1126-1133.

Mayfield, J. et al., Environmental control to reduce transmission of *Clostridium difficile*. Clin Infect Dis. 2000; 31: 995-1000.

Apisarnthanarak, A. et al., Effectiveness of environmental and infection control programs to reduce transmission of *Clostridium difficile*. Clin Infect Dis. 2004; 39: 601-2.

Hoffman, P. et al., Environmental management services project enhances infection control program. Abstracts of the Association for Practitioners in Infection Control Educational Conference and International Meeting. 2004:Phoenix, Arizona. (abstr 22353).

Falk, P. et al., Outbreak of Vancomycin-resistant *Enterococci* in a burn unit. Infect Control Hosp Epidemiol. 2000;21:575-582.

Weber, D. et al., Role of environmental contamination in the transmission of Vancomycin-resistant *Enterococci*. Infect Control Hosp Epidemiol 1997;18:306-309.

Dominguez, M. et al., Spread and maintenance of a dominant Methicillin-resistant *Staphylococcus aureus* (MRSA) clone during an outbreak of MRSA disease in a Spanish hospital. J Clin Micro. 1994;32:2081-2087.

Layton, M. et al., An outbreak of mupirocin-resistant *Staphylococcus aureus* on a dermatology ward associated with an environmental reservoir. Infect Control Hosp Epidemiol 1993;14:369-375.

Rutala, W., APIC Guidelines Committee. APIC guideline for selection and use of disinfectants. Am J Infect Control. 1996;24:313-42.

Rutala, W. et al., Susceptibility of antibiotic-susceptible and antibiotic-resistant hospital bacteria to disinfectants. Infect Control Hosp Epidemiol.1997;18:417-21.

Centers for Disease Control and Prevention/Healthcare Infection Control Advisory Committee (HICPAC), Guidelines for Environmental Infection Control in Healthcare Facilities: Recommendations of CDC and the Healthcare Infection Control Practices Advisor Committee (HICPAC), Atlanta, GA: Centers for Disease Control and Prevention; 2003. Available at www.cdc.gov. Accessed Dec. 20, 2004.

Department of Health, Winning ways. Working together to reduce healthcare associated infection in England. Report from the Chief Medical Officer, London: Crown Copyright;Dec. 2003 Available at www.dh.gov.uk/en/Publicationsandstatistics/Publications.

Centers for Disease Control and Prevention, Draft Guideline for Isolation Precautions; Preventing Transmission of Infectious Agents in Healthcare Settings, 2004. Federal Register 2004; 69: 33034.

Carling, P. et al., An Evaluation of Patient Room Cleaning in Three Intensive Care Units Using a Novel Targeting Methodology, Abstracts of the 44th Interscience Conference on Antimicrobial Agents and Chemotherapy; 2004:Washington, D.C.; p. 376 (abstr K-1601).

Noskin, G. et al., Engineering infection control through facility design. Emerg Infect Dis.2001;7:354-356.

Widmer, A. et al., Alcohol-based handrub: Evaluation of technique and microbiological efficacy with international Infection Control professionals. Infect Control Hosp Epidemiol. 2004;25:207-209.

Kim, P. et al., Rates of hand disinfection associated with glove use, patient isolation and changes between exposure to various body sites. Am J Infect Control. 2003; 31: 97-103.

Pyrek, K., Infection prevention through proper hand hygiene and gloving. Infect Control Today. 2004; 7: (10) 44-47.

Kampf, G. et al., Epidemiologic background of hand hygiene and evaluation of the most important agents for scrubs and rubs. Clin Microbial Reviews. 2004;863-893.

Farr, B. et al. Can antibiotic-resistant nosocomial infections be controlled? Lancet Infect Dis.2001;1:38-45.

Muto, C. et al., Shea Guideline for preventing nosocomial transmission of multidrug-resistant strains of *Staphylococcus aureus* and *Enterococcus*. Infect Control Hosp Epidemiol. 2003;24:362-386.

Farr, B., For nosocomial vancomycin-resistant *Enterococcal* infections; the ounce of prevention or the pound of cure? Clin Infect Dis. 2004; 38:1116-8.

Slaughter, S. et al., A comparison of the effect of universal use of gloves and gowns with that of glove use alone on acquisition of Vancomycin-resistant *Enterococci* in a medical intensive care unit. Ann Intern Med. 1996;125:448-456.

Diekema, D., Use of active surveillance cultures to control Vancomycin-resistant *Enterococcus*.Clin Infect Dis. 2003;37:1400-1403.

Jackson, M. et al., HICPAC/SHEA—conflicting guidelines: What is the standard of care? Am J Infect Control. 2004;32:504-511.

Nijssen, S. et al., Are active microbiological surveillance and subsequent isolation needed to prevent the spread of Methicillin-resistant *Staphylococcus aureus*? Clin Infect Dis. 2005;40:405-409.

Tiemersma, E. et al., Methicillin-resistant *Staphylococcus aureus* in Europe, 1999-2002. Emerg Infect Dis. 2004;10:1627-1634.

Boyce, J. et al., Controlling Vancomycin-resistant *Enterococci*. Infect Control Hosp Epidemiol.1995;16:634-637.

Nath, S. et al., A sustained outbreak of *Clostridium difficile* in a general hospital: Persistence of a toxigenic clone in four units. Infect Control Hosp Epidemiol.1994;15:382-389.

Stiefel, U. et al., Increased susceptibility to Vancomycin-resistant *Enterococcus* intestinal colonization persists after completion of anti-anaerobic antibiotic treatment in mice. Infect Control Hosp Epidemio 20041; 25:373-379.

Livornese, L. et al., Hospital-acquired infection with vancomycin-resitant *Enterococcus faecium* transmitted by electronic thermometers. Ann Intern Med.1992;117:112-116.

Centers for Disease Control and Prevention, Recommendations for preventing the spread of vancomycin resistance: recommendations of the Hospital Infection Control Practices Advisory Committee (HICPAC). MMWR; 1995;44:1-13.

Gould, F. et al., Nosocomial infection with microsphere beds. The Lancet. 1993;342:241-242.

Sheretz, R. et al., A cloud adult: the *Staphylococcus aureus*-virus interaction revisited. Ann Intern Med. 1996; 124: 539-547.

Donskey, C., The Role of the intestinal tract as a reservoir and source for transmission of nosocomial pathogens. Clin Infect Dis. 2004;39:219-26.

Rutala, W. et al., New disinfection and sterilization methods. Emerg Infect Dis. 2001;7:348-353.

Smith, T. et al., Environmental contamination with vancomycin-resistant *Enterococci* in an outpatient setting. Infect Control Hosp Epidemiol 1998;19:515-518.

Linkin, D. et al., Risk factors for extended-spectrum beta-lactamase-producing enterobacteriaceae in a neonatal intensive are unit. Infect Control Hosp Epidemiol 2004;25:781-783.

Griffith, C. et al., Environmental surface cleanliness and the potential for contamination during handwashing.Am J Infect Control 2003;31:93-96.

Rutala, W. et al., Surface disinfection: Should we do it? J Hosp Infect. 2001; 48 (supplement A): S64-S68.

Hota, B. et al., Contamination, colonization and cross-colonization: Are hospital surfaces reservoirs for nosocomial infection? Clin Infect Dis; 39:1182-9.

Kim et al., Isolation of *Clostridium difficile* from the Environment and Contacts of Patients with Antibiotic-Associated Colitis, J. Infect Dis., 1981:143:42-50.

Malik, R. et al., Use of audit tools to evaluate the efficacy of cleaning systems in hospitals. Am J Infect Control 2003;31:181-187.

Diekema, D. et al., Antimicrobial trends and outbreak frequency in United States hospitals. Clin Infect Dis; 38:78-85.

Julia Louise Gerberding, MD, MPH, Hospital-Onset Infections: A Patient Safety Issue. American College of Physicians—American Society of Internal Medicine. vol. 137, No. 8, 665-670, Oct. 28, 2002.

John M. Boyce, MD et al., Do Infection Control Measures Work for Methicillin-Resistant *Staphyloococcus aureus*?—Infection Control and Hospital Epidemiology. vol. 25, No. 5, 395-40 May 2004.

Robert A. Weinstein Controlling Antimicrobial Resistance in Hospitals: Infection Control and Use of Antibiotics—Emerging Infections Diseases, vol. 7, No. 2, 188-192, Mar.-Apr. 2001.

Marlene Wullt et al., Activity of Three Disinfectants and Acidified Nitrite Against *Clostridium difficile* Spores—Infection Control and Hospital Epidemiology, vol. 24, No. 10, 765-768, Oct. 2003.

Arjun Srinivasan, A Prospective Study to Determine Whether Cover Gowns in Addition to Gloves Decrease Nosocomial Transmission of Vancomycin-Resistant *Enterococci* in an Intensive Care Unit—Infection Control and Hospital Epidemiology, 424, Aug. 2002.

Rory Van et al. Environmental Contamination in Child Day-Care Centers—American Journal of Epidemiology, vol. 133, No. 5, 460-470, 1991.

Carling et al., A Prospective Evaluation of Patient Room Cleaning in Two Hospitals Using a Novel Targeting Methodology—Society for Healthcare Epidemiology of America, Abstract Control No. 04-A-127-SHEA, 2 pages, as submitted Jan. 2004 (not published until Apr. 19, 2004, see Reference DV).

Carlinge et al., A Prospective Evaluation of Patient Room Cleaning in Two Hospitals Using a Novel Targeting Methodology—The Fourteenth Annual Scientific Meeting of the Society for Healthcare Epidemiology of America, No. 237, p. 103, Apr. 2004.

Struellens, M. et al., Control of Nosocomial Transmission of *Clostridium difficile* Based on Sporadic Case Surveillance, Am. J. Med., vol. 91 (Suppl. 3B), pp. 138S-143S (Sep. 16, 1991).

Shay, D. et al., Epidemiology and Mortality Risk of Vancomycin-Resistant *Enterococcal* Bloodstream Infections, J. Infect. Dis., pp. 993-1000 (1995).

Rampling, A. et al., Evidence that hospital hygiene is important in the control of methicillin-resistant *Staphylococcus aureus*, J. Hosp. Infect., pp. 109-116 (2001).

Griffith C. et al., An evaluation of hospital cleaning regimes and standards, J. Hosp. Inf., pp. 19-28 (2000).

Bonten, M. et al., Epidemiology of colonization of patients and environment with vancomycin-resistant *Enterococci*, Lancet, vol. 348, pp. 1615-1619 (Dec. 14, 1996).

Wullt, M. et al., Activity of Three Disinfectants and Acidified Nitrite Against *Clostridium difficile* Spores. Infect. Control Hosp. Epidemiol, pp. 765-768 (2003).

* cited by examiner

Contaminated Surfaces

| | VRE | MRSA | C. Difficile |
|---|---|---|---|
| Bed Rails | ++++++ | + | +++ |
| Bed Table | ++++++ | + | |
| Door Knobs | ++ | ++ | + |
| Doors | +++ | + | |
| Call Button | +++ | + | ++ |
| Chair | ++ | + | ++ |
| Tray Table | +++ | ++ | |
| Toilet Surface | + | | ++++ |
| Sink Surface | + | + | +++ |
| Bedpan Cleaner | | | + |

FIG. 1

Survival of Pathogens on
Environmental Surfaces

C. Difficile - > 5 months
MRSA - 90 to > 236 d.
VRE - 7 to 120 d.
E. coli O 157 - > 60 d.

Rhinoviruses - Several Hours
Hepatitis A - > 4 hours
Parainfluenza viruses - 10 hours Target After Marking

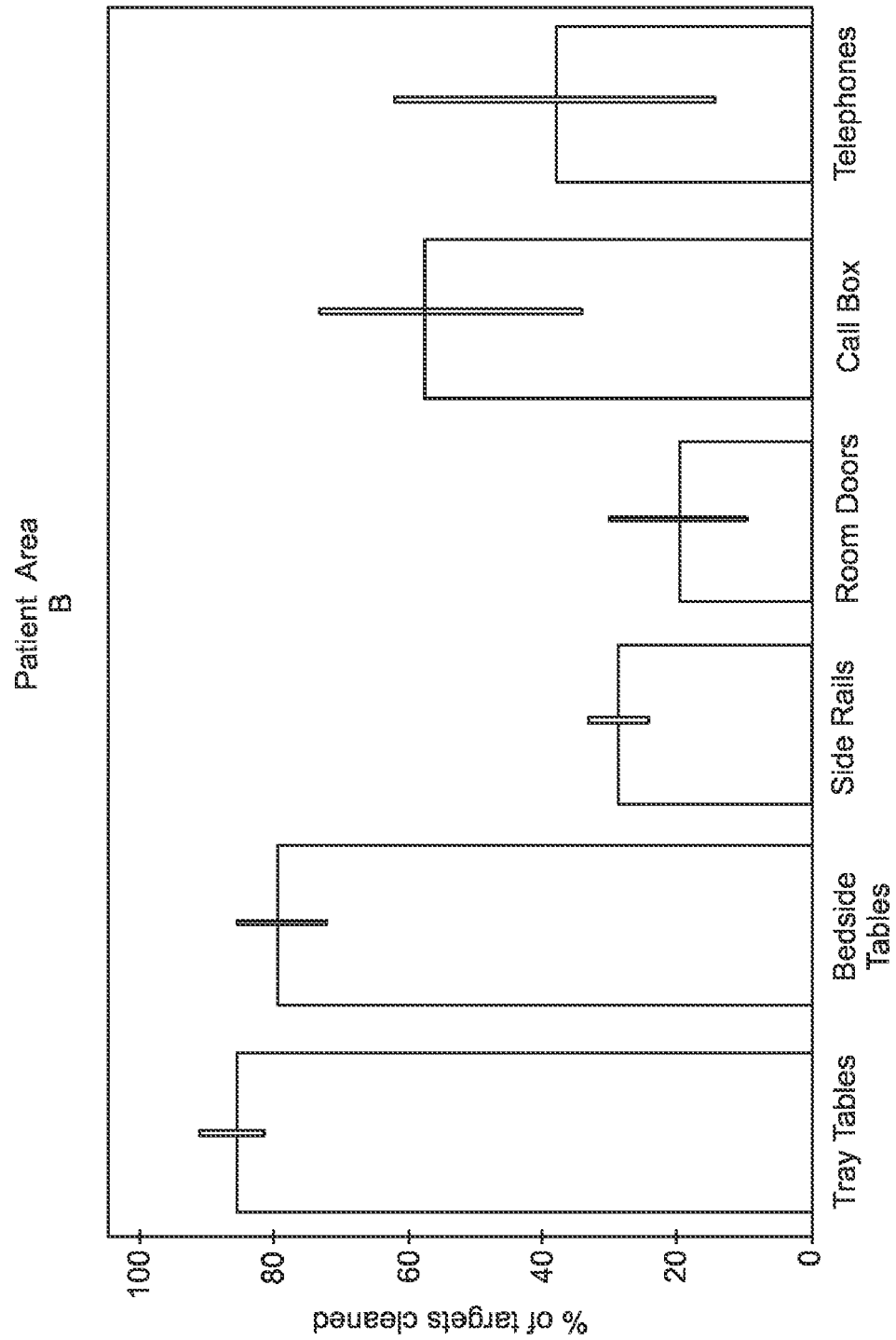
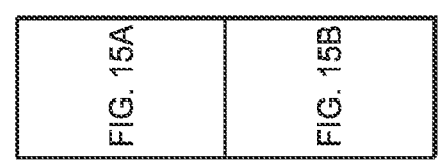
FIG. 14
FIG. 15

EnviroCheck Systems

Level I Participant Program

1100

1120 → Environmental Evaluation        (Phase 1)

A. Introduction training. ( ICP - 1.5 hr.)
        EnviroCheck Systems overview
        Role of near patient environment in infection prevention
        Evaluation technology B. Pre-intervention data collection ( ICP - 3.0 hr. over 4 weeks)

C. Intra-institutional comparison and evaluation.

D. Programmatic support.-Ongoing

1140 → Program Enhancement        (Phase II)

A. Administrative leadership[1] education related to Phase I and agreement to develop a Quality Improvement action plan.

B. Completion of Participant Agreement

C. Site specific Demographic Data Set collection ( ICP - 1.0 hr.)

D. Senior hospital administration[2] educational intervention related to Phase I ( ICP - 1.0 hr.)

E. Environmental services staff[3] educational intervention related to Phase I* ( B - D above ) ( ICP 2.0 hr.)

F. Implementation of targeted Cleaning and Disinfect ion Program. ( ICP - 1.0 hr.)

G. Evaluation of initial intervention program.[4] ( ICP - 2.0 hr. over 4 weeks )

FIG. 15A

H. Administrative and Environmental Service Feedback of pre/post intervention results, including :

1. General administration presentation. (ICP - 1.0 hr.)

2. Graphic feedback to environmental services. (Excel templates provided) (ICP - 1.0 hr.)

3. Graphic feedback to nursing units. (Excel templates provided) (ICP - 1.0 hr)

I. Further programmatic evaluation - (ICP - 2.0 over 4 wk.)

J. Programmatic feedback (as in H above) (ICP - 1.0 hr.)

K. Assistance with JCAHO Presentation

1160 → PROGRAM COMPARISION   (Phase III)

A. Programmatic evaluation - ongoing (ICP 2.0 hr. each 6 months)

B. Programmatic feedback (as in H above) (ICP 1.0 - hr. each 6 months)

C. Inter-Institutional comparison - ongoing (1.0 hr. every months)

D. Administrative feedback ongoing through Infection Control Committee.

E. Programmatic and individual recognition.

F. Consideration of other applications.

FOOTNOTES

1. Directors of Quality Assurance, Patient Care and usually the Director of Environmental Services, although it may be better for the ICP to educate and enlist the support of the latter individual separately.

2. The Senior Hospital Leadership Group Group which goes by different terms at different hospital.

3. To include all supervisor and personnel from all shifts.

4. Done three to four weeks after program implementation complete.
   * Power Point program template provided

FIG. 15B

MONITORING CLEANING OF SURFACES

PRIORITY

The present application claims priority from the U.S. Provisional Patent Application 60/666,391, filed Mar. 30, 2005, which is hereby incorporated herein by reference in its entirety.

TECHNICAL FIELD

The present invention relates to monitoring cleaning of surfaces, and, more particularly, to monitoring cleaning of surfaces in health care environments.

BACKGROUND

Although environmental cleaning and disinfecting practices have become a cornerstone of patient care, assessment of actual compliance with such procedures has not been reported. During the past decade controlling and limiting the spread of health care associated pathogens has become one of the most challenging and aspects of health care epidemiology. Unfortunately the continuing escalation of infections with these pathogens has led to more than 1.5 million people developing resistant hospital acquired, i.e., nosocomial, infections in the U.S. annually. Despite enhancement of hand hygiene through the development of user friendly alcohol based hand cleansers, the manner in which they are used and the difficulty achieving appropriate compliance with their use potentially limit their effectiveness.

Three pathogens posing significant nosocomial problems are MRSA (Methicillin Resistant *Staphylococcus aureus*), VRE (Vancomycin Resistant *Enterococcus*), and *Clostridium difficile* (*C. difficile*). Their importance derives from a combination of resistance to presently available treatments and an ability to rapidly spread extensively in the environment around hospitalized patients. MRSA is present in wound infections, as associated with bed sores and catheters. VRE is present in bowel and urinary tract infections. *C. difficile* is also present in bowel infections and presents as severe diarrhea. For each of these pathogens, control with present antibiotics is problematical, if not impossible.

Although screening based isolation practices have been advocated to limit the transmission of MRSA and VRE, there are logistical issues and concerns about the practical application and cost effectiveness of such practices. Reliance on such practices may alter the epidemiology but not the incidence of health care associated infections. Additionally, outbreak persistence as well as significant environmental contamination occurs despite patients being on isolation for VRE and MRSA as well as for patients who are asymptomatically colonized with *C. difficile* for which screening is not feasible. These programmatic as well as pathogen based issues clearly have limited the effectiveness of current as well as proposed isolation practices.

Enhancement of existing cleaning and disinfection practices deserves further consideration and evaluation. Although it is not currently feasible to define the independent role of the hospital environment in the transmission of health care associated pathogens except in isolated investigations, numerous studies over the past twenty years have confirmed the frequent contamination (FIG. 1) of many surfaces in the near patient environment (FIG. 2) with hospital associated pathogens able to survive on inanimate surfaces for weeks to months (FIG. 3).

With respect to individual pathogens, it has been found that high rates of environmental contamination with *C. difficile* have been associated both with symptomatic as well as asymptomatic patients. Direct evaluation of the role of environmental contamination in the transmission of *C. difficile* found a strong correlation with the intensity of environmental contamination, and outbreaks of *C. difficile* infection have been successfully terminated by enhanced cleaning/disinfecting activities.

The role of environmental contamination in transmission of VRE has been documented. Recent studies have confirmed the frequency of environmental contamination, shown to be highly correlated with the number of body sites colonized as well as with the intensity of gastrointestinal tract colonization. Furthermore the ease with which gloved hands can become contaminated by limited contact with a colonized patient's bed rail and bedside table the rapid recontamination of surfaces in the near patient environment with VRE despite effective daily cleaning even in the absence of diarrhea as well as the termination of a VRE outbreak in an ICU through enhanced cleaning activities support the likely importance of the environment in the epidemiology of VRE.

MRSA is frequently found in the environment of both colonized and infected patients and colonized health care workers. The pathogen can be transmitted by the gloves of health care providers and increases in concentration in the stool of colonized patients receiving broad spectrum antibiotics. Consequently, it is likely that environmental contamination plays a role in the spread of MRSA. In addition, DNA typing in three studies has supported the likely importance of environmental reservoirs in colonal MRSA outbreaks in hospitals lasting from three months to five years.

These and similar observations confirm the longstanding belief that environmental cleaning/disinfecting activities are important in providing an optimally safe environment for patients and have led to the development of specific guidelines for environmental infection control in health care facilities. Environmental disinfecting does work. Materials such as phenolic compounds, quartinary ammonium compounds, chloride disinfectants, and formaldehyde can kill a wide range of microbial pathogens, work rapidly, and work effectively in clinical settings as shown in FIG. 4.

In 2002, the Centers of Disease Control (CDC) recommended that hospitals "thoroughly clean and disinfect environmental medical equipment surfaces on a regular basis". Similarly, the Society for Health Care Epidemiology of America's position paper regarding enhanced interventions to control the spread of resistant *Staphylococcus aureus* and *Enterococcus* recommended that hospitals "ensure" that their institutional methods of disinfecting surfaces be shown to be "adequate". In 2003, the National Health Service of Great Britain specifically recommended that "cleaning and disinfecting programmes and protocols for environmental surfaces in patient care areas should be defined".

Most recently the draft guidelines for isolation precautions developed by the CDC in 2004 emphasize the importance of environmental cleaning and disinfection activities. Draft guidelines for isolation precautions developed by the CDC emphasize the importance of environmental cleaning and disinfection activities. Although these guidelines specifically state that hospitals "ensure compliance by housekeeping staff with cleaning and disinfecting procedures" and "insure consistent cleaning and disinfection of surfaces in close proximity to the patient and likely to be touched by the patient and health care worker", they provide no directives regarding the means by which hospitals are to assist their ability to comply with or "insure" the effectiveness of such activities prospectively.

In a similar manner the Joint Commission for Health Care Accreditation 2004 standard states "hospitals are expected to develop standards to measure staff and hospital performance in managing and improving the environment of care" without defining what specific resources should be utilized to carry out such activities.

In view of the above, there is a need for a non-microbiological methodology to evaluate the thoroughness with which housekeeping activities are carried out in hospitals.

SUMMARY OF THE INVENTION

In accordance with one aspect of the invention, a method for monitoring cleaning of a surface includes applying an amount of transparent indicator material to an area of a surface and measuring the amount remaining on the surface. The transparent indicator material may be fixed to the area of the surface, as by drying. The transparent indicator material may be a fluorescent material and measuring the amount of remaining on the surface may include exposing the area to ultraviolet radiation.

Some embodiments may include one or more opportunities for reducing the amount of the transparent indicator material whose location may be unknown to the receiver of the opportunity. Reducing the amount may be a part of cleaning the surface. The opportunity to reduce the amount of transparent indicator material may be suspended at the expiration of a period of time following initiation, where the period may be a day or less, between a day and a week, or between a week and a month.

In accordance with another aspect of the invention, a composition for monitoring cleaning of a surface includes a carrier, a transparent indicator soluble in the carrier, a transparent source of adherence to the surface soluble in the carrier, and a surfactant. In certain embodiments, the carrier may be soluble in water and the carrier may be a detergent. In other embodiments the transparent indicator may be fluorescent under ultraviolet radiation. In additional embodiments, the transparent source of adherence may be a natural glue such as methyl cellulose.

In accordance with a further aspect of the invention, a method for control of nosocomial pathogens includes evaluating a cleaning program for a patient-care environment within a facility, enhancing the cleaning program for the patient care environment, and comparing the enhanced cleaning program with at least one other cleaning program. In certain embodiments, evaluating a cleaning program may include training with monitoring surfaces, collecting pre-intervention data, and comparing control within the facility.

In other embodiments, enhancing the cleaning program may include collecting site-specific demographic data, providing education to administrative leadership, senior hospital administration and environmental services staff, implementing a targeted cleaning and disinfection program, evaluating an initial intervention program, obtaining feedback of pre and post intervention results, and assisting with a presentation to the Joint Commission on Accreditation of Healthcare Organizations (JCAHO).

In additional embodiments, comparing the cleaning program may include comparing cleaning within the facility with cleaning within at least one other facility.

BRIEF DESCRIPTION OF THE DRAWINGS

The foregoing features of the invention will be more readily understood by reference to the following detailed description, taken with reference to the accompanying drawings, in which:

FIG. 1 illustrates frequency of contamination of common hospital room locations by three pathogens.

FIG. 14 illustrates results of monitoring of a patient area of a hospital room.

FIG. 15 illustrates a method for control of nosocomial pathogens.

DETAILED DESCRIPTION OF SPECIFIC EMBODIMENTS

Definitions. As used in this description and the accompanying claims, the following terms shall have the meanings indicated, unless the context otherwise requires:

Terminal cleaning refers to cleaning of a hospital room following departure of its most recent occupant and prior to the arrival of its immediately prospective occupant.

Black light refers to ultraviolet or UV radiation emanating from an ultraviolet source.

Transparent refers to capable of transmitting light so that objects and images beyond can be clearly perceived.

Nosocomial infections are infections arising from and transmitted within a hospital environment.

Cleaning of patient rooms is an ongoing process in a hospital. Each patient occupying a room may be subject to pathogens left by a prior occupant of the room and, in turn, may insert his or her specific pathogens into the room environment. An aim of room cleaning is to decrease the likelihood of the environmental transmission of infection to an occupant of the room. Some room sites are cleaned daily while others are cleaned following patient occupation. Generally, such cleaning is unsupervised. Correlation of the health of room occupants could provide an indication of the quality of the cleaning, although with significant effort and with significant delay.

Embodiments of the invention as discussed below illustrate where monitoring may provide timely assessment as to whether current cleaning activities are consistent with control over nosocomial infections and may have the potential for objectively evaluating cleaning and disinfecting activities in various health care settings. A nontoxic composition containing an indicator material which fluoresces with exposure to a black light is inconspicuous yet may be readily removed by housekeeping products. Small volumes of composition may be confidentially applied to target sites in patient rooms following terminal cleaning and the targets reevaluated following terminal cleaning after several patients have occupied the room.

In an example, evaluation of housekeeping practices at three hospitals have confirmed high rates of cleaning of traditional sites but poor cleaning of many sites which have significant potential for harboring and transmitting microbial pathogens. An integrated program may identify such deficiencies in hospital cleaning and target remediation efforts so as to accelerate reduction in pathogen levels.

Figure 2:
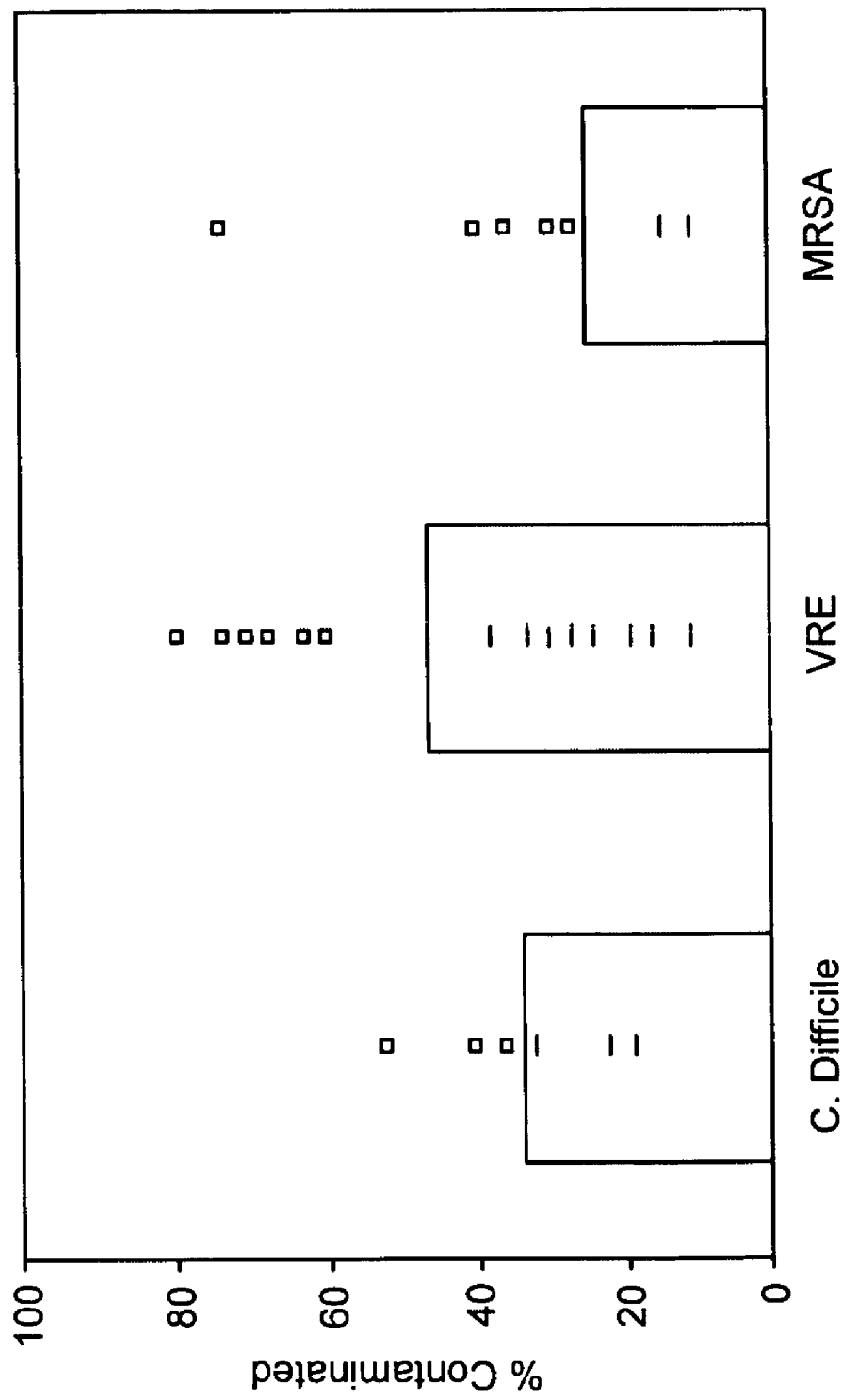
FIG. 2 illustrates the percentage of contamination of hospital surfaces by the pathogens of FIG. 1.
Figures 3, 4:
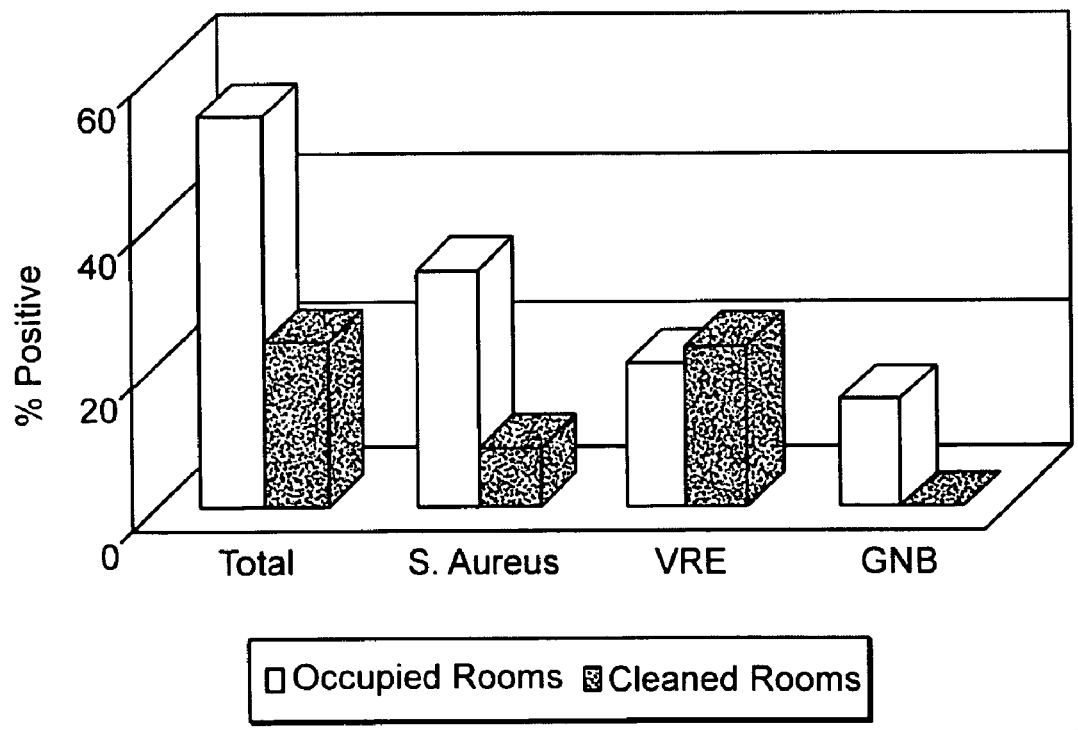
FIG. 3 illustrates survival of pathogens on inanimate surfaces.
FIG. 4 illustrates a microbiologic evaluation of patient room contamination and disinfection.
Figure 5:
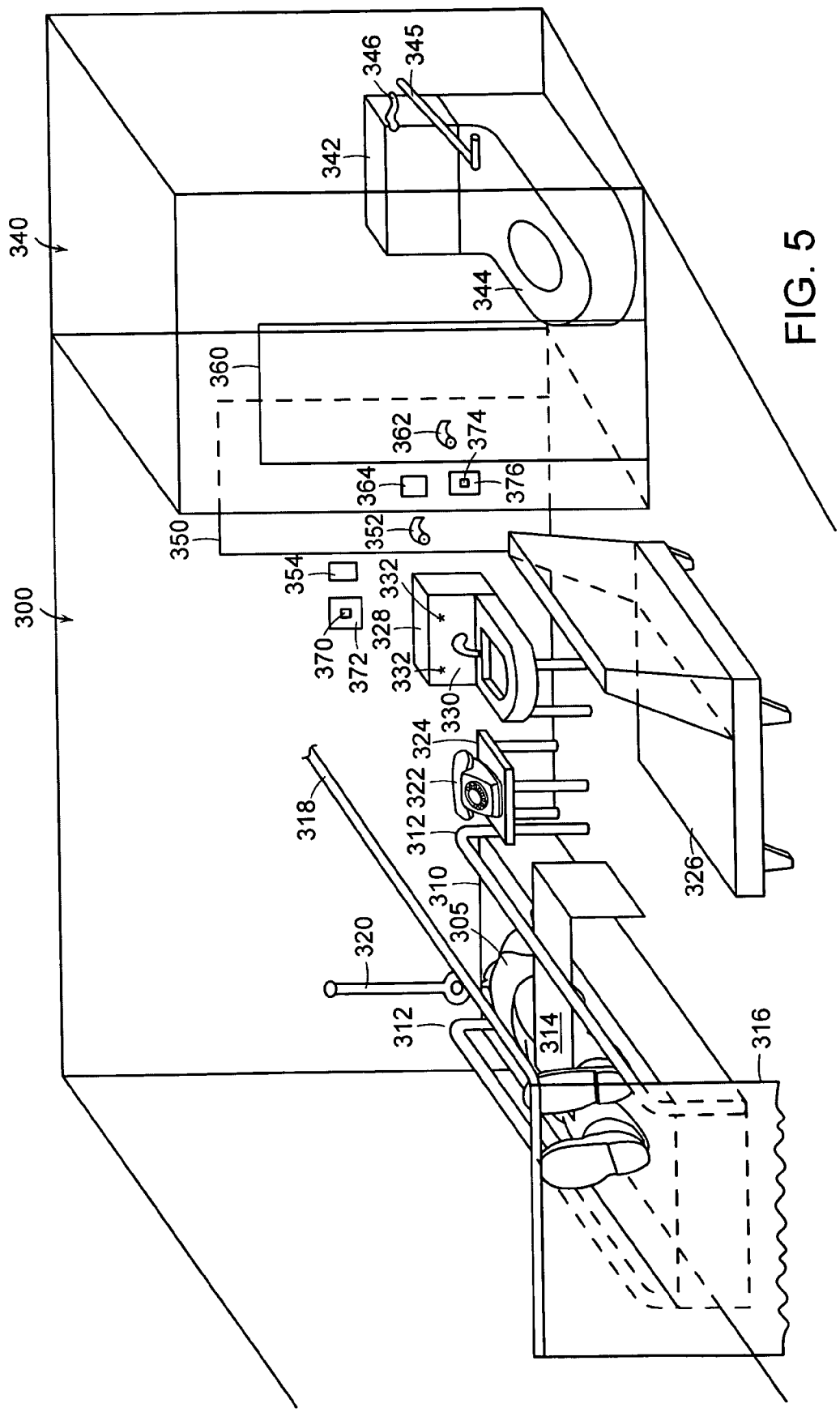
FIG. 5 illustrates the contents of a typical hospital room.

FIG. 5 illustrates a typical hospital room 300. Room 300 contains bed 310 in association with bed rails 312, bed tray 314, drape 316, and drape support 318. Patient call box 320 and telephone 322 are located proximal to bed 310 and provide communication, where telephone 322 rests on table 324. Chair 326 provides additional seating. Sink 328 including faucet 330, handles 332, and bedpan flushing device 334 provide a cleansing facility. Toilet 342 containing seat 344 and handle 346 resides in bathroom 340. Grab bar 348 provides support for patient 305 in using the toilet 342. Entry into room 300 and bathroom 340 is through doors 350 and 360 respectively via engagement of handle 352 or push plate 354 for door 350 and of handle 362 or push plate 364 for door 360. Room lights are adjusted by room light switch 370 mounted on room light switch plate 372. Bathroom lights are adjusted by bathroom light switch 374 mounted on bathroom light switch plate 376.

Figure 6:
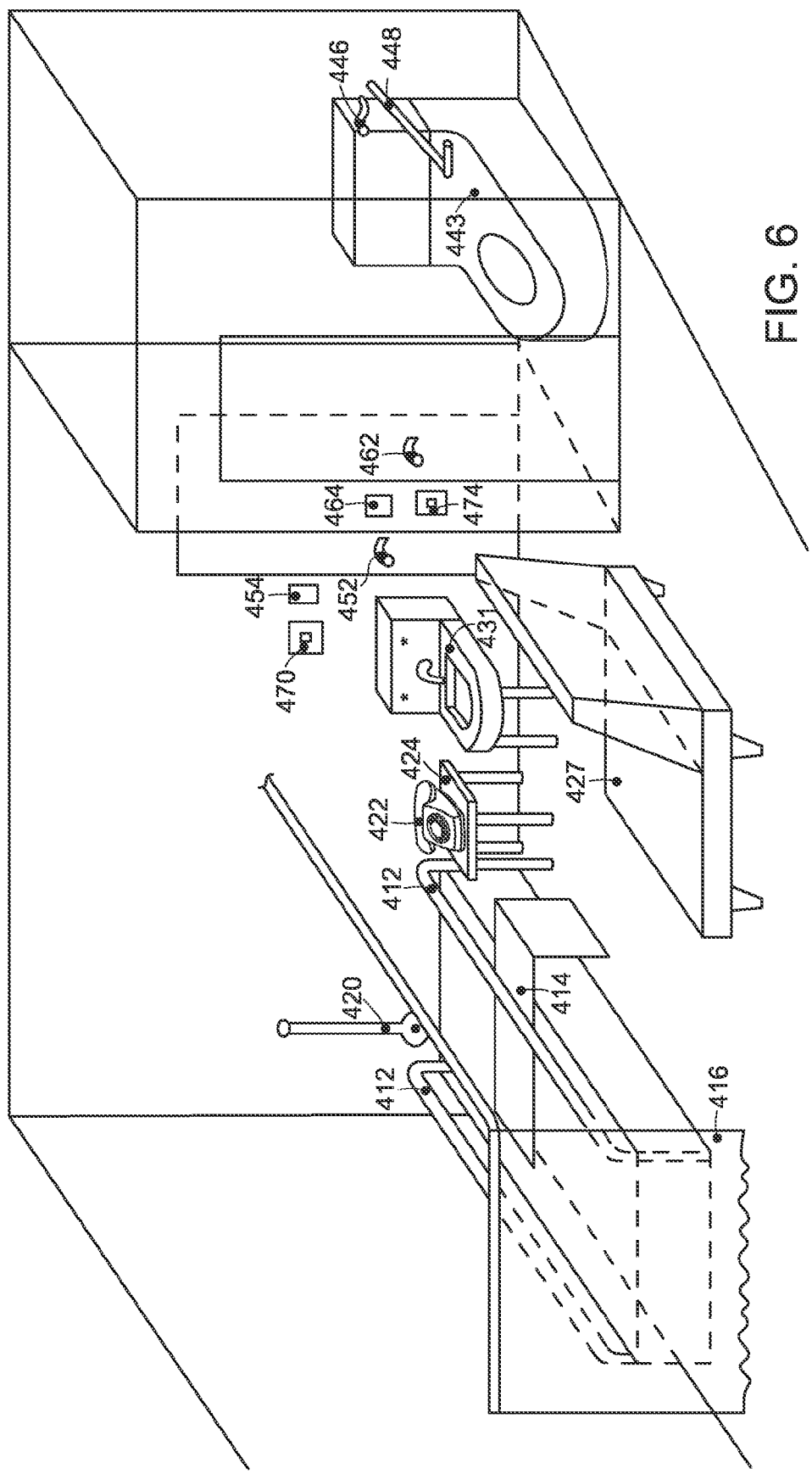
FIG. 6 illustrates typical locations of targets within a hospital room.

FIG. 6 illustrates targets for monitoring. These targets correspond to areas of a surface and may be chosen on the basis of the recommendation from the CDC that enhanced cleaning activities should be directed at "high touch" objects (HTOs), as well on reports in the literature of sites reported as being frequently contaminated with hospital associated pathogens. Such targets may include toilet handle target 446, horizontal surface target 443 of toilet bowl 342, bedpan flushing device target 434, horizontal surface target 431 of the sink 328 adjacent to the faucet 330, doorknob or door handle targets 452, 462 [or push/grab plate targets 454, 464], toilet area hand hold target 448 immediately adjacent to the toilet 342, bedside table target 424, telephone receiver target 422, call button target 420, overbed table target 414, seat target 427 of patient chair 326, bedrail target 412 adjacent to the head of the bed 310, drape target 416, room light switch target 470, and bathroom light switch target 474.

Figure 7:
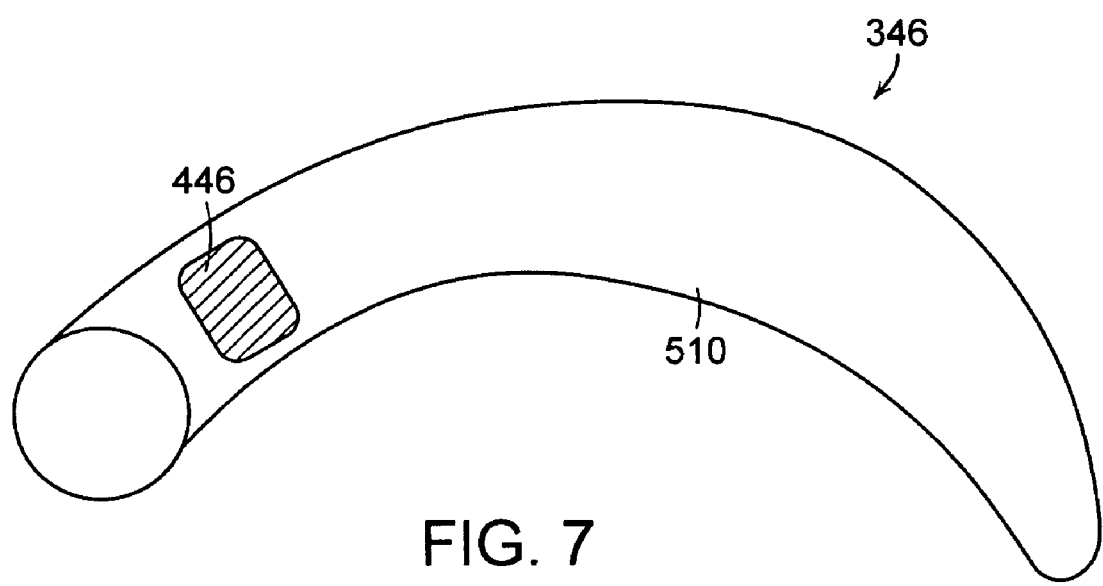
FIG. 7 illustrates a target located on a toilet handle.

To the degree possible, targets may be placed on the object to be monitored in an area which is easily accessible for cleaning and in close proximity to the portion of the object most frequently contaminated by patients' and health care workers' hands. As a consequence of this separation, indicator material placed on the targets is not subject to removal by the actions of the patient during the interval between placement of the indicator and the subsequent examination of the target. In addition, proximity of the targets to areas subject to patient contact makes probable that cleaning of the targets correlates with cleaning of the patient contact areas. For example, FIG. 7 illustrates location of toilet handle target 446 on toilet handle 346 that is separated from, but in the proximity of, region 510, the area most likely to receive patient contact during use and be contaminated.

Figure 8:
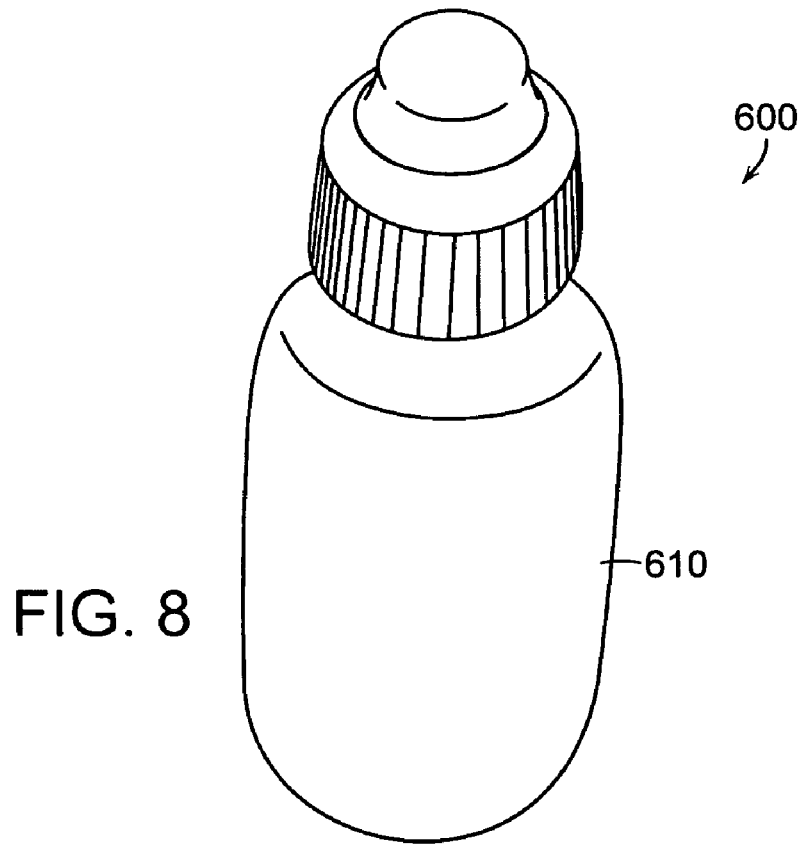
FIG. 8 illustrates a dispenser of a composition containing transparent indicator material.

FIG. 8 illustrates an applicator 600 for controllably applying a composition or targeting solution 610 for monitoring cleaning of a target such as toilet target 446. In FIG. 8, the applicator 600 is a plastic squeeze bottle. The composition 610 may be inconspicuous as by transparency, environmentally stable, and nontoxic, dry rapidly, be readily wetted by spray disinfectants, and be easily removed with light abrasion.

The composition 610 may include a carrier, a transparent indicator soluble in the carrier, a transparent source of adherence to the surface soluble in the carrier, and a surfactant. The carrier may be a biodegradable anionic or nonionic surfactant containing ammonium laureth sulfate, cocamide mea, cocamidopropyl betaine, ammonium laureth sulfate, sodium lauryl sulfate lauramide DEA, glycerine or sodium pareth-23 sulfate. The carrier may, in one embodiment, comprise between 35% and 55% percent of the composition. In one embodiment, the carrier may comprise 45% of the composition.

The transparent indicator may be a transparent ink such as Invisible Ink™ containing fluorescent blue/red water based tracer that is fluorescent under ultraviolet radiation. The transparent indicator, in one embodiment, may comprise between 3% and 5% of the composition. In one embodiment, the transparent ink may comprise 4% of the composition.

The transparent source of adherence may be a natural glue such as methyl cellulose or ethyl cellulose which may be available as powders. The source of adherence may, in one embodiment, comprised between 38% and 58% of the composition. In one embodiment, the source of adherence may comprise 48% of the composition.

The transparent surfactant may be polypropylene glycol with p-tert-octylphenoxy polyethoxyethyl alcohol (such as Photo-Flo™). In one embodiment, the transparent surfactant may comprise between 0.5% and 1.5% of the composition. In one embodiment, the transparent surfactant may comprise 1% of the composition.

Prior to cleaning of a room, the composition or targeting solution may be deposited on targets such as those indicated in FIG. 6 and fixed to the surface, as, for example, by being allowed to dry. Since the dried composition does not occupy a location likely to encounter abrasion from daily activities, its removal may be assumed to be the result of cleaning activities. When the dried targeting solution is transparent, those engaged in cleaning activities are unaware of target locations. Consequently, they are not biased to clean areas adjacent to the targets and to avoid non-adjacent areas.

Figure 9:
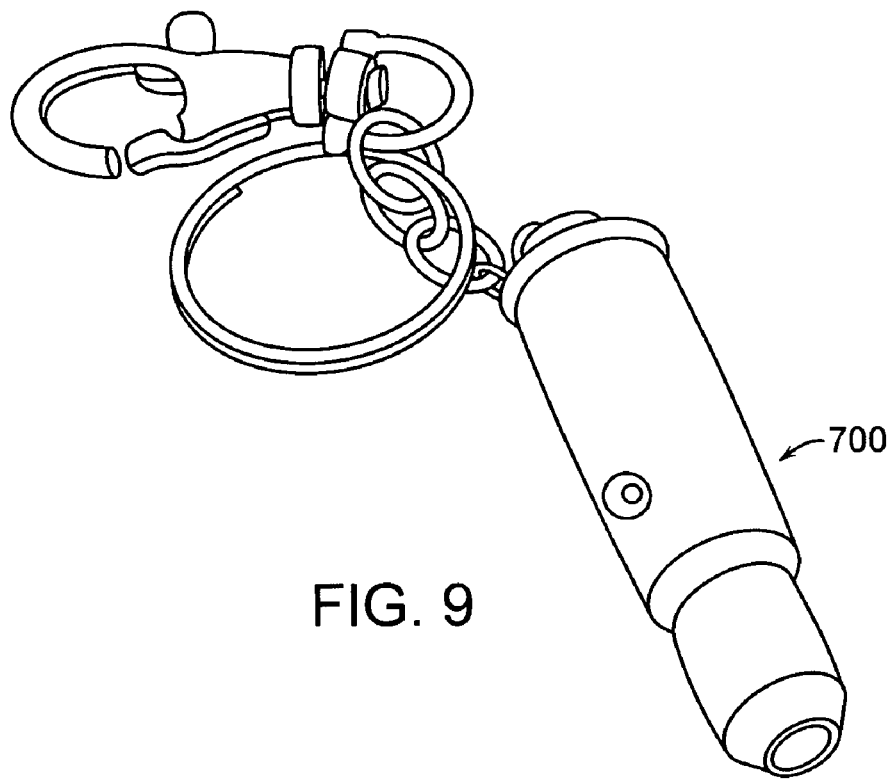
FIG. 9 illustrates a source of ultraviolet radiation.
Figure 10A:
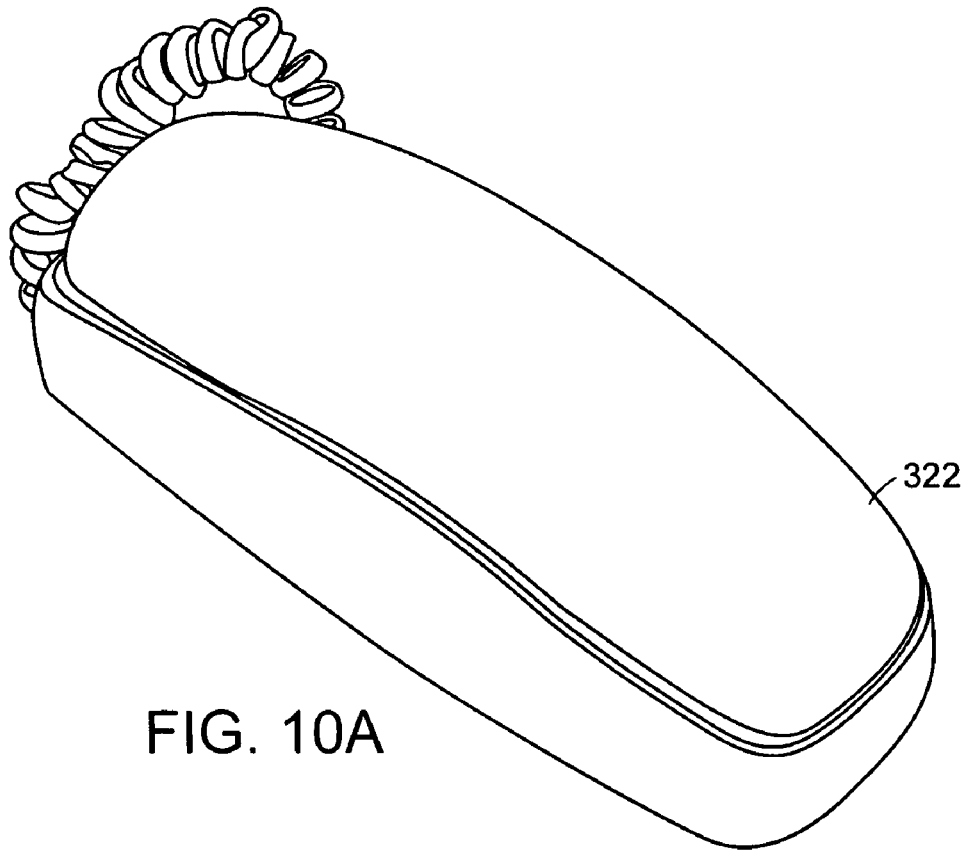
FIGS. 10A and 10B illustrate detection of a transparent indicator material using a source of ultraviolet radiation.
Figure 10B:
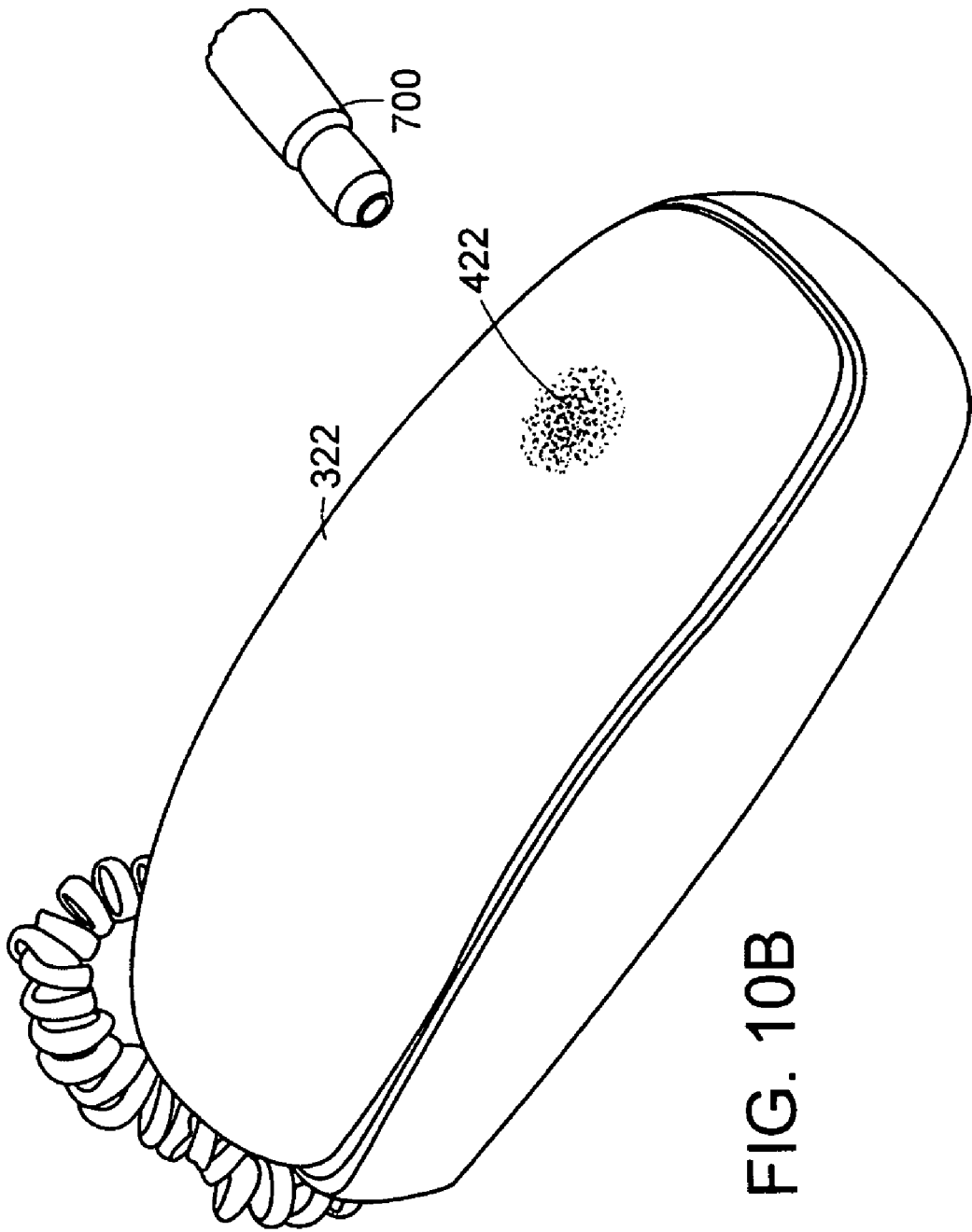

After a single cleaning opportunity or multiple cleaning opportunities are presented, cleaning activities may be suspended. That is, further cleaning in the room may not be permitted until the target areas are scanned. The targets within a room may be then scanned with a device able to render visible the dried composition so as to reveal the extent to which the targets have been subjected to cleaning. A target may be considered to have been cleaned if the dried composition was removed or clearly disturbed. If the composition contains a material fluorescent under exposure to ultraviolet radiation, a UV source 700 as shown in FIG. 9 may be held over the target locations to reveal dried composition not removed during cleaning FIG. 10A shows the lack of visibility of a telephone receiver target 422 comprising fluorescent material on a telephone receiver 322 prior to cleaning under ordinary room illumination and FIG. 10B shows the visibility of the same target 422 under ultraviolet illumination from UV source 700, also prior to cleaning. If the transparent fluorescent material is Invisible Ink™ (Blacklight World), then an ultraviolet or UV source such as ULTRA9800 Ultra Mini Portable Black Light™ (Zigzagalightware) may permit observation of dried composition residues.

A study of hospital cleaning activities employing the above method, materials, and equipment has revealed deficiencies in cleaning.

Two of the hospitals involved in the study had similar demographics. They were both urban primary and secondary care institutions. Hospital A had 136 and hospital B had 115 medical/surgical beds with 15 and 14 bed combined medical/surgical intensive care units. Although the hospitals have geographic proximity, their administrative, clinical and housekeeping staffs are completely independent. Hospital C was a 60 bed acute care short-term rehabilitation hospital.

A targeting solution was used that contained an environmentally stable nontoxic base to which was added a chemical marker as a transparent indicator which fluoresced brightly when exposed to a black light, i.e. ultraviolet light. The targeting solution dried rapidly on surfaces to leave a residue that was inconspicuous, remained environmentally stable for several weeks, resisted dry abrasion, and was easily removed with moisture accompanied by minimal abrasion. Small plastic squeeze bottles were used to dispense approximately 0.2 ml. of solution to standardized target sites.

A group of 12 targets were chosen on the basis of the CDC's recommendation that enhanced cleaning activities should be directed at "high touch" surfaces [46], as well as sites reported in the previously cited literature as being frequently contaminated with hospital associated pathogens. Such surfaces included toilet handles, the horizontal surface of toilet bowls, bedpan flushing devices, horizontal surface of sinks adjacent to a faucet, doorknobs (or push/grab plates), toilet area hand holds immediately adjacent to the toilet, bedside tables, telephone receivers, call buttons, overbed tables, the seats of patient chairs and frequently contacted areas on bedrails. To the degree possible, the targeting material was placed on the high touch object (HTO) in an area which was easily accessible to cleaning and in close proximity to that portion of the object most frequently contacted by patients' and health care workers' hands.

HTOs were confidentially marked after a room had been terminally cleaned following discharge of its occupant. After two to three patients had occupied the room and the room was again terminally cleaned, a handheld black light was used to determine if the marked HTOs in the room had been cleaned. While the marking material was usually completely removed by routine disinfection cleaning, the object was considered cleaned if the target material was clearly disturbed. Patient room floors and room walls were not evaluated given the limited potential for their serving as a source of transmission of nosocomial pathogens [50]. Statistical data analysis was performed using a two tailed Fisher's exact test.

Figure 11:
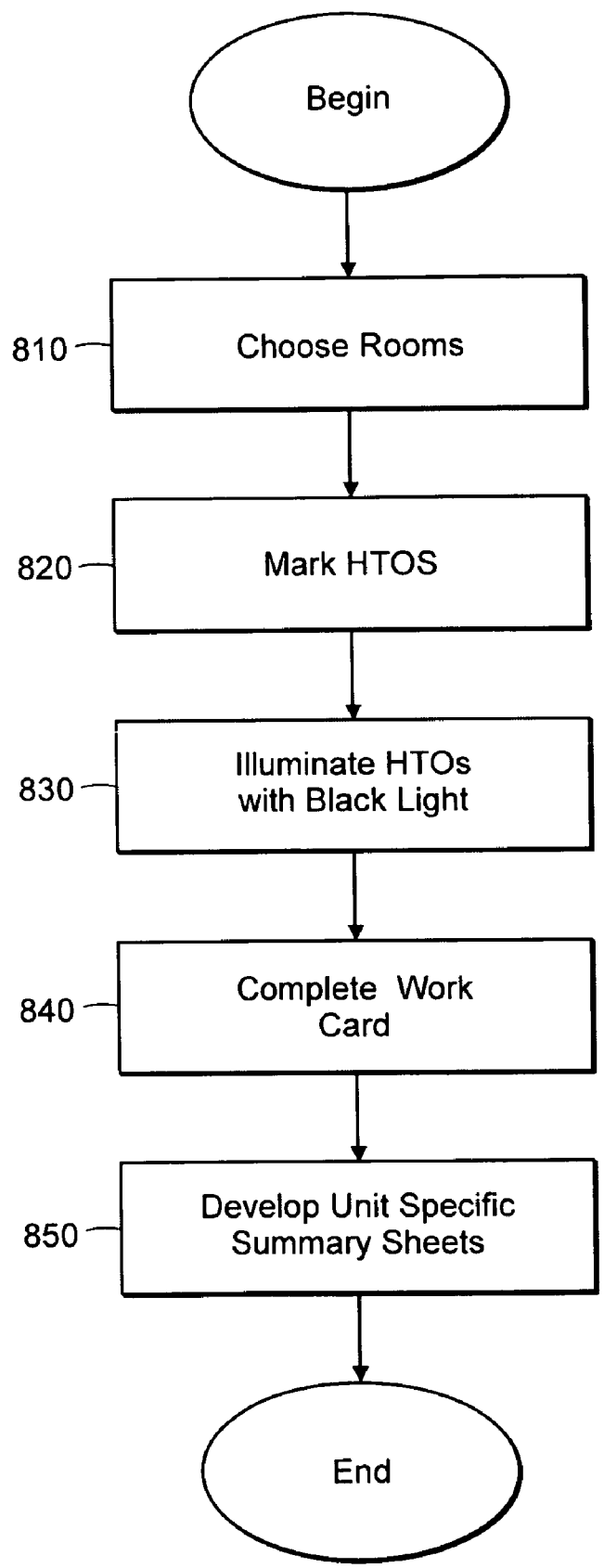
FIG. 11 illustrates a method for pre-intervention data collection.

FIG. 11 illustrates a method 800 for pre-intervention data collection. In step 810, rooms for evaluation are chosen randomly with representation from all medical/surgical (M/S) and intensive care (ICU) patient care units. In step 820, HTOs are confidentially marked after a room had been terminally cleaned following discharge of its occupant. At the time a target is marked, a standardized work card (supplied) is developed noting the date, room location and the HTOs marked. In step 830, after two to three patients have occupied the room and the room is again terminally cleaned on two or three occasions, a handheld black light is used to determine if the marked HTOs in the room have been cleaned. While the marking material is usually completely removed by routine disinfection cleaning, an object may be considered cleaned if the target material is clearly disturbed. In step 840, the work card is dated and completed on the basis of the observations made. In step 850, once between 50 and 60 rooms are evaluated, Unit Specific Summary Sheets (supplied) are developed to facilitate data analysis.

Figure 12:
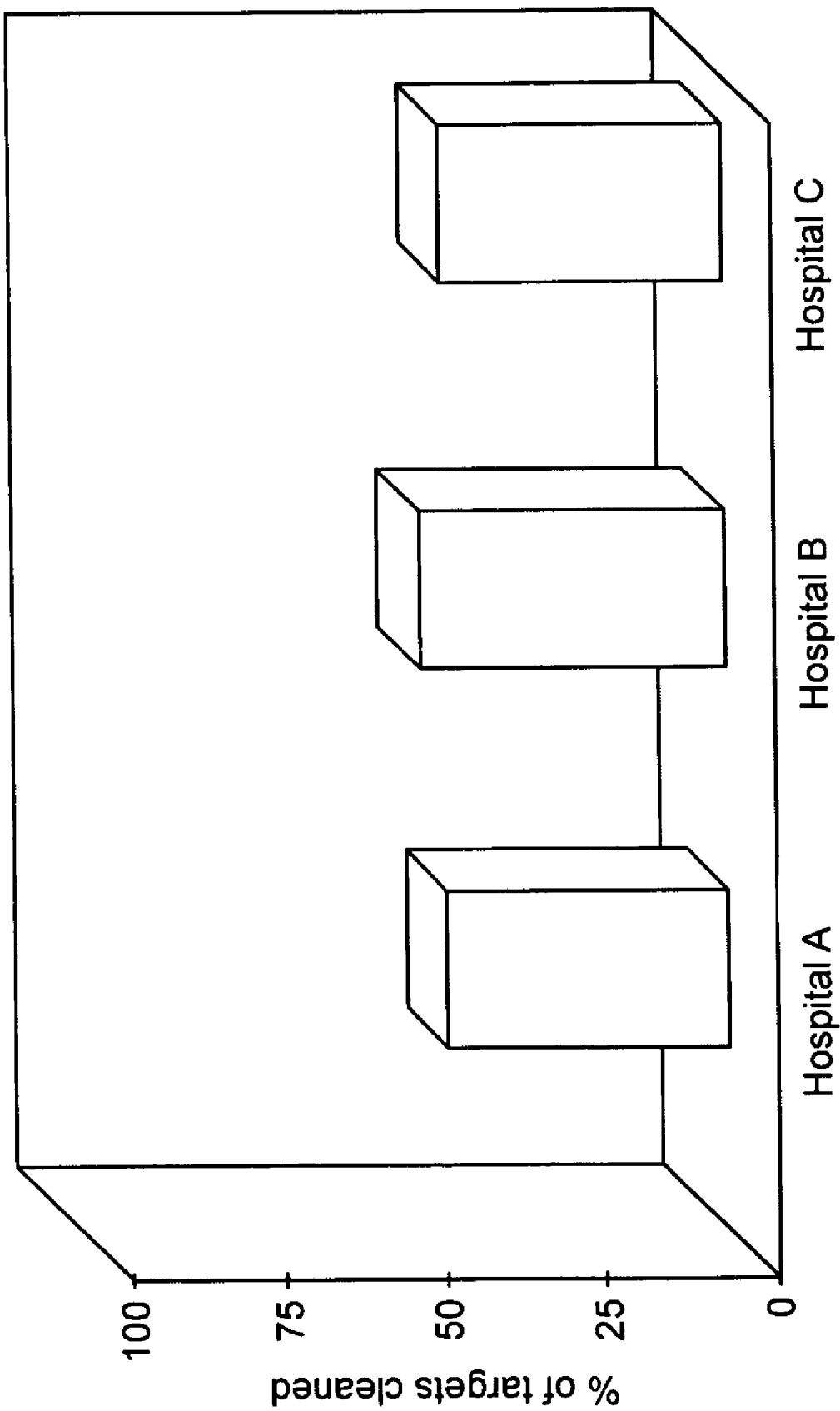
FIG. 12 illustrates results of monitoring the cleaning activities of three hospitals.
Figure 13:
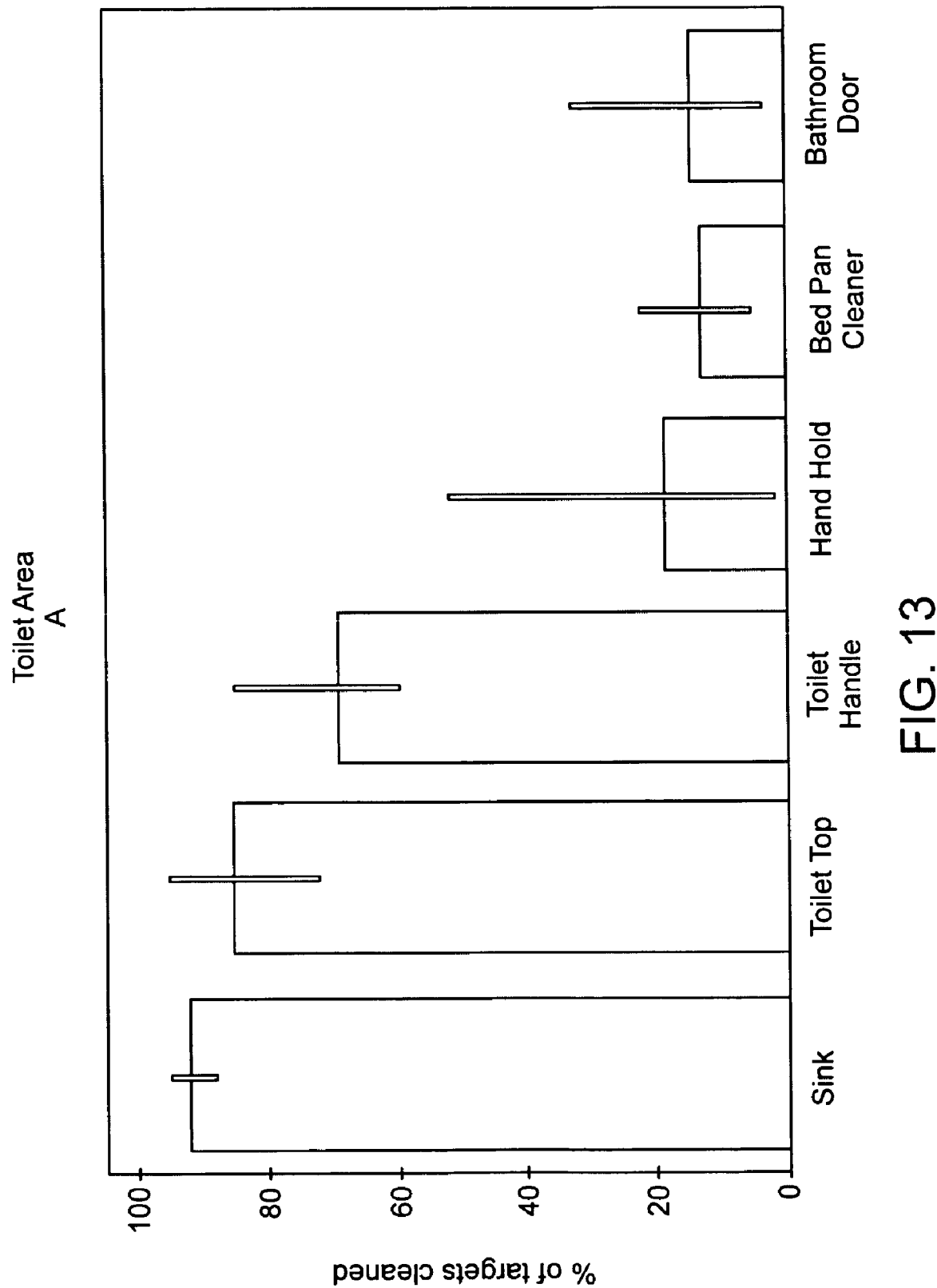
FIG. 13 illustrates results of monitoring of a toilet area of a hospital room.

During the study of periods ranging from one to four months, 60, 54 and 43 rooms were evaluated at the three hospitals respectively. Overall 47% of the 1404 HTOs evaluated were found to have been cleaned after several terminal cleanings. As illustrated in FIG. 12, similar rates of cleaning were found in each of the three hospitals. As illustrated in FIG. 13 for toilet areas and FIG. 14 for patient areas, high rates of cleaning, between 80% and 92%, were found for bedside tables, toilet tops, tray tables, and sinks. In contrast several HTOs, including bedpan cleaning equipment, patient room and bathroom doorknobs (or door pulls) as well as toilet handholds were cleaned in between 12.3% and 18% of rooms overall. The differences found between well cleaned objected (>80%) and poorly cleaned objects (<20%) in the three hospitals was highly significant (P=<0.001). The remaining objects, although more thoroughly cleaned than the group of poorly cleaned objects, were, as a group, still significantly less well cleaned than the objects cleaned greater than 80% of the time (mean=88.3% vs. 54.5%, P=<0.0001).

Although the CDC 2003 Guidelines for Environmental Infection Control in Healthcare Facilities recommends "cleaning and disinfection of high touch surfaces (e.g., doorknobs, bedrails, light switches in and around toilets in patients' rooms) on a more frequent schedule than minimal touch housekeeping services" (Environmental Services I, E, 3) [45], the aforementioned hospital results indicate that many of these HTOs were not cleaned as a regular part of terminal room cleaning. In view of the consistently high frequency of cleaning documented for sinks, toilet tops and tray tables, suboptimal cleaning of many HTOs such as bedpan cleaners, toilet area handholds and doorknobs may be the result of lack of appreciation for the potential role the latter objects have in the transmission of nosocomial pathogens rather than ineffective terminal disinfection cleaning in general.

Two of the least well cleaned HTOs, bedpan cleaners (mean 12.3%, range 9% to 20%) and toilet area handholds (mean 17.7%, range 0-50%), represent objects with a high potential for contamination by environmentally resilient gastrointestinal colonizing pathogens such as *C. difficile*, VRE and MRSA. In view of the effectiveness of disinfectants for a wide range of pathogens including antibiotic resistant bacteria, ineffectiveness of terminal cleaning/disinfection activities in substantially eliminating these pathogens from the near patient environment in other studies may be the result of suboptimal cleaning.

FIG. 15 illustrates a method for control of nosocomial pathogens using the above technique as facilitated by an integrated program 1100 tailored to a particular health facility such as a hospital. The program involves sequential implementation of a baseline environmental evaluation system (BEES) 1120, a program enhancement system (PES) 1140, and a program comparison system (PCS) 1160. In the BEES 1120, Infection Control Practitioner (ICP) is provided and undertakes an assessment of the effectiveness of terminal cleaning in approximately 40 randomly chosen patient rooms. Members of the health care facility are made aware of the role of near patient environment in infection prevention and of the usefulness of transparent targets. During BEES 1120, site specific demographic data and pre-intervention data are collected and comparisons made within the health care facility or health care institution.

Once the pre-intervention status has been documented in BEES 1120, target monitoring activities are launched in PES 1140. Following an opportunity for administration leadership to comment on the baseline assessment phase, specific training is given to the general facility administration and to the environmental services staff before implementation of targeted cleaning and disinfection. Following evaluation of the initial intervention, structured graphic feedback on the results of the intervention is provided to administrative, environmental, and nursing services.

Next, in PCS 1160, the program is evaluated and feedback given on an ongoing basis, for example, every six months. Part of the feedback involves comparison of the health care facility to other institutions. Recognition may be tended to individuals within the program and to the program itself for favorable comparisons with outside institutions.

Although the above discussion disclosed various exemplary embodiments of the invention, it should be apparent that those skilled in the art can make various modifications that will achieve some of the advantages of the invention without departing from the true scope of the invention.

What is claimed is:

1. A method for determining if a surface has been cleaned, the method comprising:
   applying an amount of transparent indicator material to one or more discrete target sites on one or more environmental surfaces, the amount of transparent indicator material being applied to the one or more discrete target sites on the one or more environmental surfaces with a non-contact applicator; and
   determining if any of the transparent indicator material remains on the one or more discrete target sites on the one or more environmental surfaces after one or more opportunities to clean the environmental surface by environmental services staff, thereby providing a cleanliness result.

2. A method according to claim 1, wherein the locations of the one or more discrete target sites are unknown to environmental services staff.

3. The method according to claim 1, wherein applying the transparent indicator material includes allowing at least a portion of the applied transparent indicator material to dry.

4. The method according to claim 1, wherein applying the transparent indicator material includes allowing the applied transparent indicator material to solidify.

5. The method according to claim 1, wherein the transparent indicator material is fluorescent upon exposure to UV radiation.

6. The method of claim 1, wherein the transparent indicator material includes
   a carrier;
   a transparent indicator soluble in the carrier;
   a transparent source of adherence to the surface soluble in the carrier; and
   a surfactant.

7. The method of claim 1, wherein the transparent indicator material is fluorescent under ultraviolet radiation.

8. The method of claim 1, wherein the one or more environmental surfaces are located within an environment that includes at least one of a hospital room, a hotel room, a cruise ship cabin, a pharmaceutical laboratory, and a restroom.

9. The method of claim 1, further comprising:
   categorizing the one or more environmental surfaces as cleaned or not cleaned based at least in part upon whether the transparent indicator material remains on the one or more discrete target sites on the one or more environmental surfaces after one or more opportunities to clean the one or more environmental surfaces by environmental services staff.

10. The method according to claim 1, wherein the transparent indicator material is transparent under visible light.

11. The method according to claim 10, wherein the transparent indicator material is transparent during application and after solidification.

12. A method according to claim 1 wherein the transparent indicator material resists dry abrasion.

13. A method according to claim 1, wherein the transparent indicator material, once applied, may only be removed using at least one of water and cleaning supplies.

14. A method according to claim 1, wherein the transparent indicator material has a viscosity sufficient to allow the transparent indicator material to be applied to non-horizontal surfaces.

15. A method according to claim 1, wherein the transparent indicator material is colorless.

16. The method according to claim 2, further including suspending the opportunity to clean the one or more environmental surfaces.

17. The method according to claim 4, wherein suspending the opportunity to clean occurs during a period of time following the one or more opportunities to clean the environmental surface and prior to determining if any of the transparent indicator material remains on the one or more discrete target sites.

18. The method according to claim 17, wherein the period of time is a day or less.

19. The method according to claim 17, wherein the period of time is between a day and a week.

20. The method according to claim 17, wherein the period of time is between a week and a month.

21. The method of claim 5, wherein determining if any transparent indicator material remains on the one or more discrete target sites includes exposing the one or more target sites to ultraviolet radiation.

22. The method according to claim 21, wherein a source of the ultraviolet radiation is a handheld device.

23. The method according to claim 22, wherein the handheld device is a black light.

24. The method according to claim 23, wherein the black light is directional.

25. The method of claim 6, wherein the transparent source of adherence to the surface is a natural glue.

26. The method of claim 25, wherein the natural glue is methyl cellulose.

27. A method for enhancing the cleaning of environmental surfaces within an environment, the method comprising:
   applying a amount of transparent indicator material to one or more discrete target sites on one or more environmental surfaces, the amount of transparent indicator material being applied to the one or more discrete target sites on the one or more environmental surface with a non-contact applicator, the one or more discrete target sites being unknown to environmental services staff;
   determining if any of the transparent indicator material remains on the one or more discrete target sites on the one or more environmental surfaces after one or more opportunities to clean the environmental surface by environmental services staff by exposing the one or more discrete target sites to ultraviolet radiation, the transparent indicator material fluorescing under the ultraviolet radiation if the transparent indicator material remains on the one or more discrete target sites;
   categorizing the one or more environmental surfaces as cleaned or not cleaned based at least in part upon whether the transparent indicator material remains on the one or more discrete target sites on the one or more environmental surfaces after one or more opportunities to clean the one or more environmental surfaces by environmental services staff, thereby providing a cleanliness result for each of the one or more environmental surfaces;

training environmental services staff on cleanliness issues, wherein training includes providing environmental services staff with information regarding at least one selected from the group consisting of improved cleaning techniques, the cleanliness result, a baseline cleanliness result, locations of areas to be cleaned, and information relating to the transmission of pathogens; and repeating the applying, determining, and categorizing steps after training environmental services staff, thereby providing a post-training cleanliness result and on-going monitoring of the cleanliness.

28. The method according to claim 27, wherein a source of the ultraviolet radiation is a directional black light.

29. A method according to claim 27, wherein the transparent indicator material resists dry abrasion.

30. A method according to claim 27, wherein the transparent indicator material, once applied, may only be removed using at least one of water and cleaning supplies.

31. A method according to claim 27, wherein the transparent indicator material has sufficient viscosity to allow the transparent indicator material to be applied to non-horizontal surfaces.

32. A method for enhancing the cleaning of a surface, the method comprising:

applying an amount of transparent indicator material to one or more discrete target sites on one or more environmental surfaces, the amount of transparent indicator material being applied to the one or more discrete target sites on the one or more environmental surfaces with a non-contact applicator;

determining if any of the transparent indicator material remains on the one or more discrete target sites on the one or more environmental surfaces after one or more opportunities to clean the environmental surface by environmental services staff, thereby providing a cleanliness result; and comparing the cleanliness result with a baseline cleanliness result.

33. The method according to claim 1 further comprising: training environmental services staff on cleanliness issues.

34. The method according to claim 32, further including providing the environmental services staff with the cleanliness result.

35. The method according to claim 33, further comprising: repeating the applying and determining steps after training environmental services personnel, thereby providing a post-training cleanliness result.

36. The method according to claim 33, wherein training environmental services staff includes providing environmental services staff with information regarding at least one selected from the group consisting of improved cleaning techniques, the cleanliness result, a baseline cleanliness result, locations of areas to be cleaned, and information relating to the transmission of pathogens.

* * * * *

UNITED STATES PATENT AND TRADEMARK OFFICE
CERTIFICATE OF CORRECTION

| | | |
|---|---|---|
| PATENT NO. | : 7,718,395 B2 | Page 1 of 3 |
| APPLICATION NO. | : 11/335905 | |
| DATED | : May 18, 2010 | |
| INVENTOR(S) | : Carling | |

It is certified that error appears in the above-identified patent and that said Letters Patent is hereby corrected as shown below:

Please delete column 9 line 1 through column 12 line 29 and insert column 9 line 1 through column 12 line 28 as attached Signed and Sealed this
Twenty-third Day of August, 2011

David J. Kappos
*Director of the United States Patent and Trademark Office*

1140. Following an opportunity for administration leadership to comment on the baseline assessment phase, specific training is given to the general facility administration and to the environmental services staff before implementation of targeted cleaning and disinfection. Following evaluation of the initial intervention, structured graphic feedback on the results of the intervention is provided to administrative, environmental, and nursing services.

Next, in PCS 1160, the program is evaluated and feedback given on an ongoing basis, for example, every six months. Part of the feedback involves comparison of the health care facility to other institutions. Recognition may be tended to individuals within the program and to the program itself for favorable comparisons with outside institutions.

Although the above discussion disclosed various exemplary embodiments of the invention, it should be apparent that those skilled in the art can make various modifications that will achieve some of the advantages of the invention without departing from the true scope of the invention.

What is claimed is:

1. A method for determining if a surface has been cleaned, the method comprising:
 applying an amount of transparent indicator material to one or more discrete target sites on one or more environmental surfaces, the amount of transparent indicator material being applied to the one or more discrete target sites on the one or more environmental surfaces with a non-contact applicator; and
 determining if any of the transparent indicator material remains on the one or more discrete target sites on the one or more environmental surfaces after one or more opportunities to clean the environmental surface by environmental services staff, thereby providing a cleanliness result.

2. A method according to claim 1, wherein the locations of the one or more discrete target sites are unknown to environmental services staff.

3. The method according to claim 2, further including suspending the opportunity to clean the one or more environmental surfaces.

4. The method according to claim 3, wherein suspending the opportunity to clean occurs during a period of time following the one or more opportunities to clean the environmental surface and prior to determining if any of the transparent indicator material remains on the one or more discrete target sites.

5. The method according to claim 4, wherein the period of time is a day or less.

6. The method according to claim 4, wherein the period of time is between a day and a week.

7. The method according to claim 4, wherein the period of time is between a week and a month.

8. The method according to claim 1, wherein applying the transparent indicator material includes allowing at least a portion of the applied transparent indicator material to dry.

9. The method according to claim 1, wherein applying the transparent indicator material includes allowing the applied transparent indicator material to solidify.

10. The method according to claim 1, wherein the transparent indicator material is fluorescent upon exposure to UV radiation.

11. The method of claim 10, wherein determining if any transparent indicator material remains on the one or more discrete target sites includes exposing the one or more target sites to ultraviolet radiation.

12. The method according to claim 11, wherein a source of the ultraviolet radiation is a handheld device.

13. The method according to claim 12, wherein the handheld device is a black light.

14. The method according to claim 13, wherein the black light is directional.

15. The method of claim 1, wherein the transparent indicator material includes
 a carrier;
 a transparent indicator soluble in the carrier;
 a transparent source of adherence to the surface soluble in the carrier; and
 a surfactant.

16. The method of claim 15, wherein the transparent source of adherence to the surface is a natural glue.

17. The method of claim 16, wherein the natural glue is methyl cellulose.

18. The method of claim 1, wherein the transparent indicator material is fluorescent under ultraviolet radiation.

19. The method of claim 1, wherein the one or more environmental surfaces are located within an environment that includes at least one of a hospital room, a hotel room, a cruise ship cabin, a pharmaceutical laboratory, and a restroom.

20. The method of claim 1, further comprising:
 categorizing the one or more environmental surfaces as cleaned or not cleaned based at least in part upon whether the transparent indicator material remains on the one or more discrete target sites on the one or more environmental surfaces after one or more opportunities to clean the one or more environmental surfaces by environmental services staff.

21. The method according to claim 1, wherein the transparent indicator material is transparent under visible light.

22. The method according to claim 21, wherein the transparent indicator material is transparent during application and after solidification.

23. A method according to claim 1 wherein the transparent indicator material resists dry abrasion.

24. A method according to claim 1, wherein the transparent indicator material, once applied, may only be removed using at least one of water and cleaning supplies.

25. A method according to claim 1, wherein the transparent indicator material has a viscosity sufficient to allow the transparent indicator material to be applied to non-horizontal surfaces.

26. A method according to claim 1, wherein the transparent indicator material is colorless.

27. A method for enhancing the cleaning of environmental surfaces within an environment, the method comprising:
 applying a amount of transparent indicator material to one or more discrete target sites on one or more environmental surfaces, the amount of transparent indicator material being applied to the one or more discrete target sites on the one or more environmental surface with a non-contact applicator, the one or more discrete target sites being unknown to environmental services staff;
 determining if any of the transparent indicator material remains on the one or more discrete target sites on the one or more environmental surfaces after one or more opportunities to clean the environmental surface by environmental services staff by exposing the one or more discrete target sites to ultraviolet radiation, the transparent indicator material fluorescing under the ultraviolet radiation if the transparent indicator material remains on the one or more discrete target sites;
 categorizing the one or more environmental surfaces as cleaned or not cleaned based at least in part upon whether the transparent indicator material remains on the one or more discrete target sites on the one or more environmental surfaces after one or more opportunities to clean the one or more environmental surfaces by environmental services staff, thereby providing a cleanliness result for each of the one or more environmental surfaces;

training environmental services staff on cleanliness issues, wherein training includes providing environmental services staff with information regarding at least one selected from the group consisting of improved cleaning techniques, the cleanliness result, a baseline cleanliness result, locations of areas to be cleaned, and information relating to the transmission of pathogens; and repeating the applying, determining, and categorizing steps after training environmental services staff, thereby providing a post-training cleanliness result and on-going monitoring of the cleanliness.

28. The method according to claim 27, wherein a source of the ultraviolet radiation is a directional black light.

29. A method according to claim 27, wherein the transparent indicator material resists dry abrasion.

30. A method according to claim 27, wherein the transparent indicator material, once applied, may only be removed using at least one of water and cleaning supplies.

31. A method according to claim 27, wherein the transparent indicator material has sufficient viscosity to allow the transparent indicator material to be applied to non-horizontal surfaces.

32. A method for enhancing the cleaning of a surface, the method comprising:

applying an amount of transparent indicator material to one or more discrete target sites on one or more environmental surfaces, the amount of transparent indicator material being applied to the one or more discrete target sites on the one or more environmental surfaces with a non-contact applicator;

determining if any of the transparent indicator material remains on the one or more discrete target sites on the one or more environmental surfaces after one or more opportunities to clean the environmental surface by environmental services staff, thereby providing a cleanliness result; and comparing the cleanliness result with a baseline cleanliness result.

33. The method according to claim 32, further including providing the environmental services staff with the cleanliness result.

34. The method according to claim 1 further comprising: training environmental services staff on cleanliness issues.

35. The method according to claim 34, further comprising: repeating the applying and determining steps after training environmental services personnel, thereby providing a post-training cleanliness result.

36. The method according to claim 34, wherein training environmental services staff includes providing environmental services staff with information regarding at least one selected from the group consisting of improved cleaning techniques, the cleanliness result, a baseline cleanliness result, locations of areas to be cleaned, and information relating to the transmission of pathogens.

* * * * *